United States Patent [19]

Arrowsmith et al.

[11] Patent Number: 4,990,509
[45] Date of Patent: Feb. 5, 1991

[54] SULFONAMIDE ANTI-ARRHYTHMIC AGENTS

[75] Inventors: John E. Arrowsmith, Deal; Peter E. Cross, Canterbury; Geoffrey N. Thomas, Sandwich, all of England

[73] Assignee: Pfizer Inc., New York, N.Y.

[21] Appl. No.: 360,517

[22] Filed: Jun. 2, 1989

Related U.S. Application Data

[62] Division of Ser. No. 37,309, Apr. 9, 1987, Pat. No. 4,863,948.

[30] Foreign Application Priority Data

Apr. 16, 1986 [GB] United Kingdom ............... 8609331

[51] Int. Cl.$^5$ ............... A61K 31/40; A61K 31/42; A61K 31/50; C07D 209/46
[52] U.S. Cl. ............... 514/247; 514/248; 544/237; 544/239
[58] Field of Search ............... 544/237, 239; 514/247, 514/248

[56]  References Cited

U.S. PATENT DOCUMENTS

| | | | |
|---|---|---|---|
| 3,341,584 | 9/1967 | Larsen et al. | 260/501 |
| 3,478,149 | 11/1969 | Larsen et al. | 514/605 |
| 3,574,741 | 4/1971 | Gould et al. | 564/99 |
| 3,660,487 | 5/1972 | Larsen et al. | 260/501 |
| 3,758,692 | 9/1973 | Larsen et al. | 514/605 |
| 4,087,541 | 5/1978 | Eberlein et al. | 548/472 |
| 4,137,318 | 1/1979 | Eberlein et al. | 514/309 |
| 4,378,361 | 3/1983 | Schromm et al. | 514/259 |
| 4,639,408 | 1/1987 | Kraguchi | 544/237 |
| 4,820,705 | 4/1989 | Nickl | 544/239 |

FOREIGN PATENT DOCUMENTS

| | | |
|---|---|---|
| 0131302 | 1/1985 | European Pat. Off. . |
| 0164865 | 12/1985 | European Pat. Off. . |
| 4290M | 8/1966 | France . |
| 2302733 | 10/1976 | France . |
| 2363564 | 3/1978 | France . |
| 645628 | 10/1984 | Switzerland . |
| 1263987 | 2/1972 | United Kingdom . |
| 1571231 | 7/1980 | United Kingdom . |
| 2135883 | 9/1984 | United Kingdom . |

*Primary Examiner*—Mark L. Berch
*Attorney, Agent, or Firm*—Peter C. Richardson; Paul H. Ginsburg

[57] ABSTRACT

A series of novel alkanesulphonamidophenyl-N-alkyl-N-(heterocyclic-alkyl) alkylamine derivatives have been prepared, including their pharmaceutically acceptable salts. These compounds are useful in therapy as anti-arrhythmic agents and therefore, are of value in the treatment of various cardiac arrythmias. Said sulfonamide base compounds are of the formula:

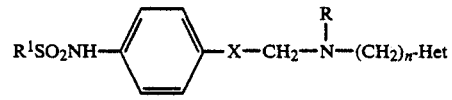

wherein R and $R^1$ are each $C_1$–$C_4$ alkyl; X is —$CH_2$—, —CO— or —CO(OH)—; n is two, three or four; and "Het—" is a nitrogen-containing heterocyclic group wherein said heterocyclic group is phenyl or benzyl-substituted 2H-pyridazin-3-on-2-yl, or it is 2H-phthalazin-1-on-2-yl, 4-halo-2H-phthalizin-1-on-2-yl or 4-($C_1$–$C_4$ alkyl)-2H-phthalazin-1-on-2-yl, 2H-isoindolin-1-on-2-yl, 3H-quinazolin-4-on-3-yl, 2H-3,4-dihydroisoquinol-1-on-2-yl, 2H-isoquinol-on-2-yl, 1H-3,4-dihydroquinol-2-on-1-yl, benzoxazol-2-on-3-yl, quinol-2-on-1-yl, quinol-2-yl or indol-2-yl, each optionally mono substituted with halogen or $C_1$–$C_4$ alkyl on the benzene portion of the respective fused ring moieties.

8 Claims, No Drawings

SULFONAMIDE ANTI-ARRHYTHMIC AGENTS

This is a division of application Ser. No. 07/037,309, filed on Apr. 9, 1984 and now U.S. Pat. No. 4,863,948.

BACKGROUND OF THE INVENTION

This invention relates to certain sulfonamides which are antiarrhythmic agents.

The compounds of the invention prolong the duration of the action potential in cardiac muscle and conducting tissue, and thereby increase refractoriness premature stimuli. Thus, they are Class III antiarrhythmic agents according to the classification of Vaughan Williams (Anti-Arrhythmic Action, E. M. Vaughan Williams, Academic Press, 1980). They are effective in atria, ventricles and conducting tissue both in vitro and in vivo and are thereof useful for the prevention and treatment of a wide variety of ventricular and supraventricular arrhythmias including atrial and ventricular fibrillation. Because they do not alter the speed at which impulses are conducted, they have less propensity than current drugs (mostly Class I) the precipitate or aggravate arrhythmias, and also produce less neurological side effects. Some of the compounds also have some positive inotropic activity and therefore are particularly beneficial in patients with impaired cardiac pump function.

SUMMARY OF THE INVENTION

Thus the invention provides compounds of the formula:

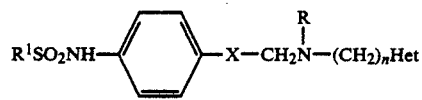
(I)

and their pharmaceutically acceptable salts,
wherein
$R^1$ is $C_1$-$C_4$ alkyl;
R is $C_1$-$C_4$ alkyl;
X is $CH_2$, CO or CH(OH);
n is 2, 3 or 4; and
Het is a 5- or 6-membered nitrogen-containing heterocyclic group which is attached to the adjacent carbon atom by a carbon or nitrogen atom and optionally contains a further heteroatom selected from O and N, said 5- or 6-membered nitrogen-containing heterocyclic group being either (i) substituted by a phenyl or benzyl group or (ii) fused at two adjacent carbon atoms to a benzene ring, said benzene ring being optionally substituted by 1 or 2 substituents each independently selected from halo and $C_1$-$C_4$ alkyl, and said 5- or 6-membered nitrogen-containing heterocyclic group being optionally substituted by up to 2 substitutents each independently selected from oxo, halo and $C_1$-$C_4$ alkyl, with the proviso that only one oxo substitutent can be present.

"Halo" means F, Cl, Br or I. $C_3$ and $C_4$ alkyl groups can be straight or branched chain.

Preferably, "Het" is a group of the formula:

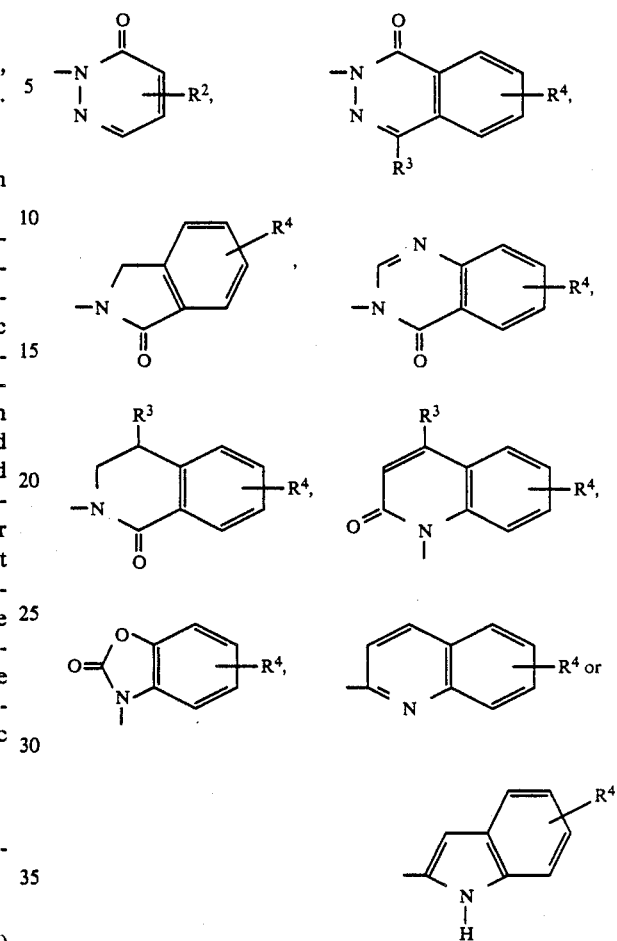

wherein $R^2$ is phenyl or benzyl; $R^3$ is H, halo or $C_1$-$C_4$ alkyl (preferably H or $CH_3$); $R^4$, which is attached to a carbon atom of the benzene ring portion, is H, halo or $C_1$-$C_4$ alkyl (preferably H, Cl or $CH_3$); and the dotted line represents an optional bond.

The most preferred groups represented by "Het" are as follows:

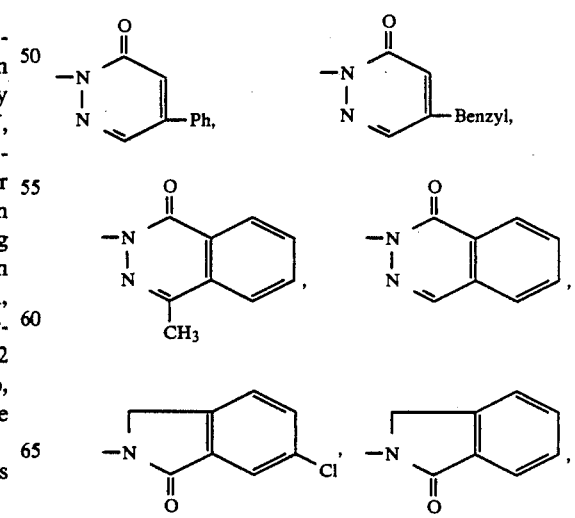

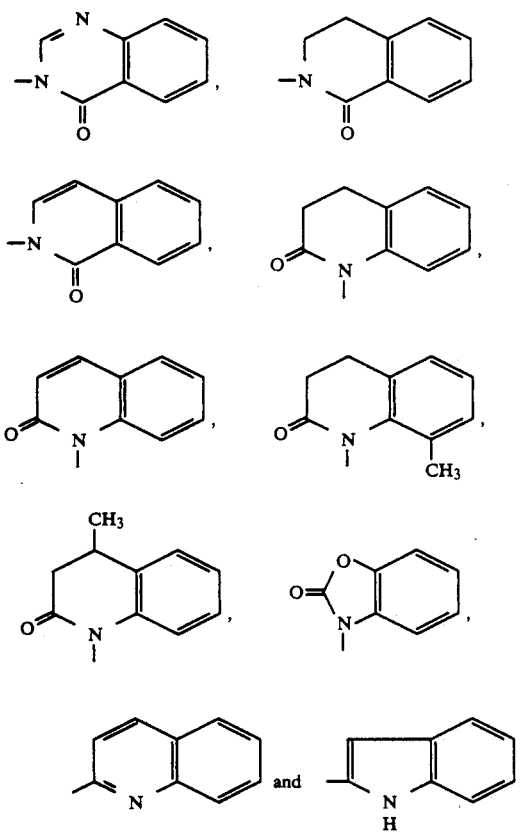

Preferably, $R^1$ is $CH_3$, R is $CH_3$ or $C_2H_5$ (most preferably $CH_3$) and n is 2 or 3 (most preferably 2).

Preferably, X is —$CH_2$— or —CH(OH)—.

A preferred individual compound has the formula:

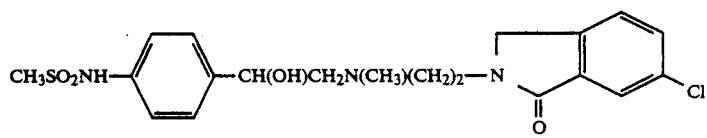

The pharmaceutically acceptable salts of the compounds of the formula (I) including acid addition salts formed from acids which form non-toxic acid addition salts containing pharmaceutically acceptable anions, such as hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, besylate and p-toluenesulphonate salts. The salts are preparable by conventional techniques.

For assessment effects of the compounds on atrial refractoriness, guinea pig right hemiatria are mounted in a bath containing physiological salt solution, and one end is connected to a force transducer. Tissues are stimulated at 1 Hz using field electrodes. Effective refractory period (ERP) is measured by introducing premature stimuli ($S_2$) after every 8th basic stimulus ($S_1$). The $S_1S_2$ coupling interval is gradually increased until $S_2$ reproducibly elicits a propagated response. This is defined as the ERP. The concentration of compound required to increase ERP by 25% ($ED_{25}$) is then determined. ERP is also measured in guinea pig right papillary muscles incubated in physiological salt solution. Muscles are stimulated at one end using bipolar electrodes and the propagated electrogram is recorded at the opposite end via a unipolar surface electrode. ERP is determined as above using the extrastimulus technique. Conduction time is obtained from a digital storage oscilloscope by measuring the interval between the stimulus artefact and the peak of the electrogram (i.e. the time required for the impulse to travel along the length of the muscle).

Atrial and ventricular ERP's are also measured in anaesthetised or conscious dogs by the extrastimulus technique whilst the atrium or right ventricle is being paced at a constant rate.

The compounds of the formula (I) can be administered alone but will generally be administered in admixture with a pharmaceutical carrier selected with regard to the intended route of administration and standard pharmaceutical practice. They can be administered both to patients suffering from arrhythmias and also prophylactically to those likely to develop arrhythmias. For example they may be administered orally in the fore of tablets containing such excipients as starch of lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as ventricular and supraventricular arrhythmias, including atrial and ventricular fibrillation, it is expected that oral dosages of the compounds of the invention will be in the range from 2 to 150 mg daily, taken in and up to 4 divided doses per day, for an average adult patient (70 kg). Dosages for intravenous administration would be expected to be within the range 1.0 to 20 mg per single dose as required. A severe cardiac arrhythmia is preferably treated by the i.v. route in order to effect a rapid conversion to the normal rhythm. Thus for a typical adult patient individual tablets or capsules might contain 2 to 50 mg of active compound, in a suitable pharmaceutically acceptable vehicle or carrier. Variations may occur depending on the weight and condition of the subject being treated as will be known to medical practitioners.

Thus the present invention provides a pharmaceutical composition comprising a compound of the formula (I) as defined above or pharmaceutically acceptable salt thereof, together with a pharmaceutically acceptable diluent or carrier.

The invention also provides a method of preventing or reducing cardiac arrhythmias in a human being, which comprises administering to said human an effective amount of a compound of the formula (I) or pharmaceutically acceptable salt thereof, or of a pharmaceutical composition as defined above.

The invention yet further provides a compound of the formula (I) or a pharmaceutically acceptable salt thereof, for use as a medicament.

The invention also provides the use of a compound of the formula (I), or a pharmaceutically acceptable salt thereof, for the manufacture of a medicament for the prevention or reduction of cardiac arrhythmias.

DETAILED DESCRIPTION OF THE INVENTION

The compounds of the formula (I) can be prepared by the following general routes:

(1) The first route to compounds in which X is —$CH_2$— or —CO— can be illustrated as follows:

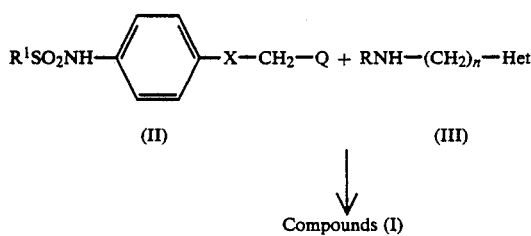

Q is a suitable leaving group, e.g. Cl, Br, I, methanesulphonyloxy, phenylsulphonyloxy or p-toluenesulphonyloxy [preferably Br], R, $R^1$, Het and n are as defined for formula (I), and X is —$CH_2$— or CO.

The reaction is preferably carried out in the presence of a base ("acid acceptor") such as triethylamine or sodium bicarbonate. Typically, the reaction is carried out in a suitable solvent, e.g., ethanol or acetonitrile at room temperature. The product can then be isolated and purified conventionally.

The starting materials of the formula (II) are either known compounds or are available conventionally as will be known to those skilled in the art.

The starting materials of the formula (III) are either known compounds or can be obtained conventionally. For example, intermediates in which "Het" is linked by a nitrogen atom to the adjacent carbon atom can be prepared as follows:

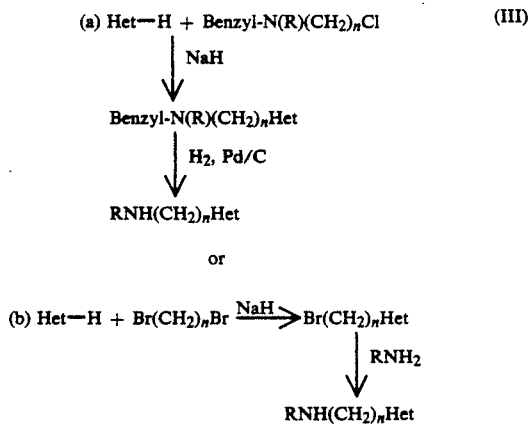

Methods (a) and (b) are illustrated in detail in the subsequent experimental section.

(2) This route to compounds in which X is —$CH_2$— or —CH(OH)— is illustrated schematically as follows:

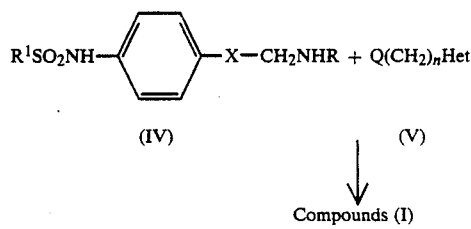

Q is a leaving group as defined in route (I) above and is preferably Br; R, $R^1$, Het and n are as defined for formula (I), and X is —$CH_2$— or —CH(OH)—.

The reaction is typically carried out in a suitable organic solvent, e.g., ethanol, and in the presence of a base ("acid acceptor"), e.g., triethylamine, sodium bicarbonate, potassium carbonate or pyridine at, say, 50°-90° C., and preferably under reflux. The product can then be isolated and purified conventionally.

The starting materials of the formula (V) are either known compounds or are obtainable conventionally, e.g. via the first step of method (b) in route (1) above.

The starting materials (IV) are again available conventionally, e.g. as follows:

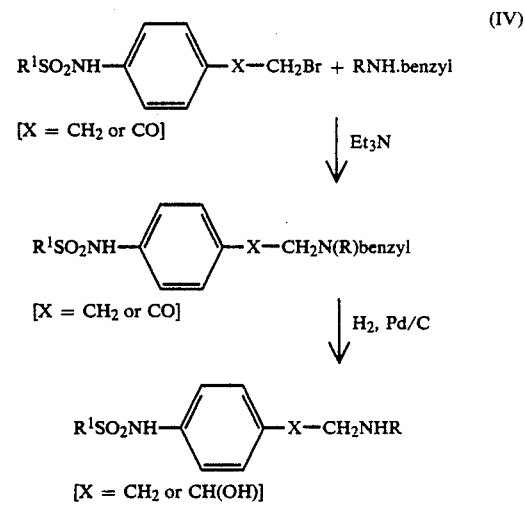

When $H_2$ over Pd/C is used for the debenzylation, this reduces a carbonyl group represented by X to —CH(OH)—.

(3) The compounds of the formula (I) in which X is $CH_2$ can also be prepared by the acylation of the corresponding amino compounds according to the following procedure:

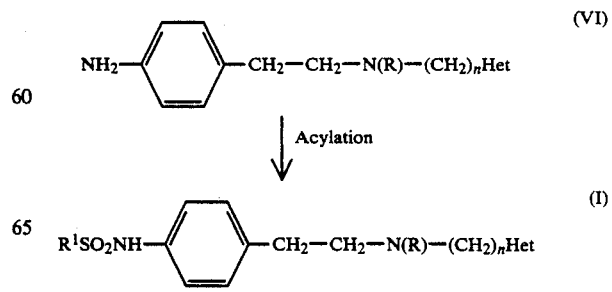

Acylation is carried out conventionally, e.g., using an acid chloride or bromide of the formula $R^1SO_2Cl$ or $R^1SO_2Br$, or an anhydride of the formula $(R^1SO_2)_2O$. The reaction is typically carried out in a suitable organic solvent, e.g., methylene chloride, at room temperature. The reaction is optionally carried out in the presence of an acid acceptor such as triethylamine, pyridine, sodium bicarbonate or potassium carbonate. The presence of an acid acceptor is preferred when a sulphonyl chloride or bromide is used as the acylating agent in which case the reaction is preferably carried out in pyridine. The product can be isolated and purified conventionally.

The starting materials (VI) are obtainable essentially by the methodology of routes (1) and (2), e.g.:

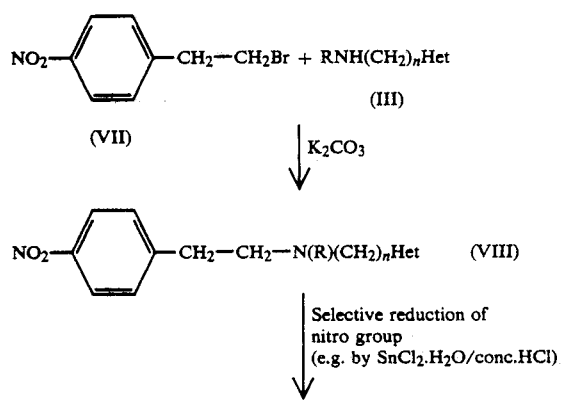

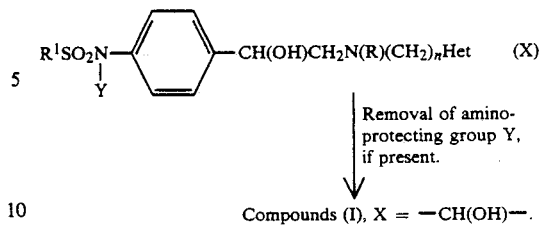

The presence of an amino-protecting group is preferred.

Typical amino-protecting groups are benzyl and t-butyl, removable, respectively, by treatment with $H_2$ over Pd/C and trifluoroacetic acid.

Benzyl is the preferred amino-protecting group.

The reaction of the oxirane (IX) with compound (III) is typically carried out in a presence of a base, e.g., triethylamine, and in s suitable organic solvent, e.g., isopropanol, at, say, 50°–90° C., and preferably under reflux. The product (X) can then be recovered and purified conventionally. Any amino-protecting group is then removed conventionally. For example, benzyl protecting groups are conveniently removed by hydrogenation in a suitable organic solvent, e.g. ethanol, containing Pd/C at, say, 50 psi and 40°–70° C. The final product can then be isolated and purified conventionally.

The starting materials (IX) can be obtained conventionally, e.g. as follows:

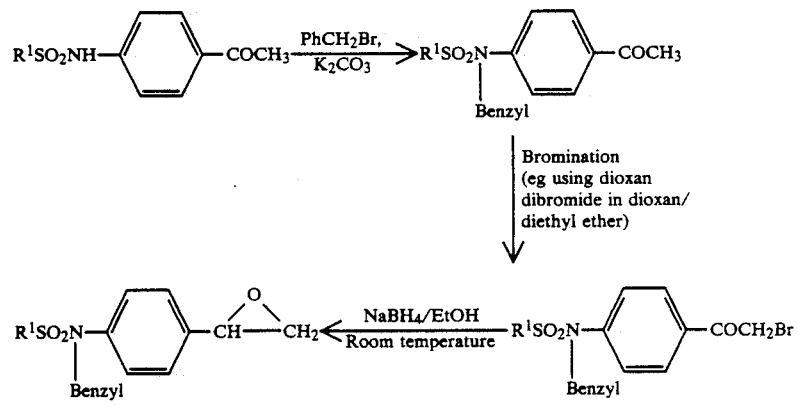

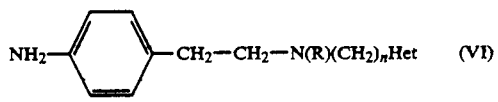

(4) The compounds of the formula (I) in which X is —CH(OH)— can also be prepared as follows:

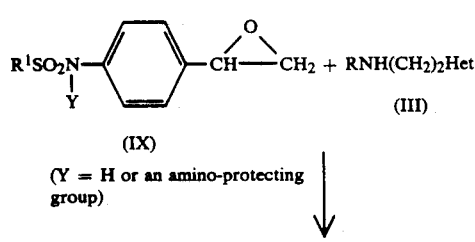

(5) The compounds of the formula (I) in which X is —CH(OH)— are however most conveniently prepared by the reduction of the corresponding carbonyl compounds (X=CO). The preferred reducing agent is sodium borohydride, the reaction being typically carried out in ethanol at room temperature. Of course, other reducing agents such as $H_2$ over a catalyst (e.g. Pd/C), $NaCNBH_3$ or $LiAlH_4$ can be used.

(6) Acid addition salts are obtainable conventionally, e.g. by reaction of a solution of the free base with ethereal hydrogen chloride or citric acid, etc., followed by recovery of the salt by filtration or evaporation of the solution.

The following Examples illustrate the invention. "50 psi" is equivalent to 344 kPa:

EXAMPLE 1

(A)

N-(4-Methanesulphonamidophenacyl)-N-methylbenzylamine

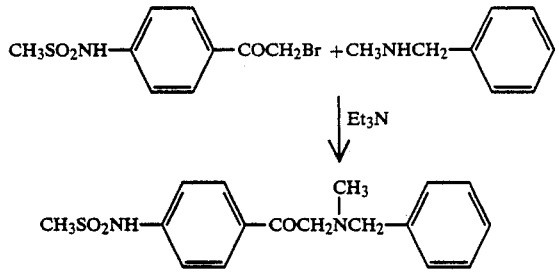

N-Methylbenzylamine (22.43 g), 4-methanesulphonamidophenacyl bromide (50 g) (see J. Med. Chem. 1966, 9, 88) and triethylamine (17 g) in ethanol (500 ml) were stirred at room temperature for 18 hours. The solvent was removed, the residue was taken up in dilute hydrochloric acid, washed with ethyl acetate and the organic layer was discarded. The aqueous layer was neutralised with sodium bicarbonate and then extracted three times with ethyl acetate. The combined organic extracts were evaporated and the residue chromatographed on silica [Merck 'Kieselgel 60' (Trade Mark)] eluting with hexane containing ethyl acetate (0% up to 100%). The title compound was obtained as an oil by collection and evaporation of appropriate fractions.

The oil solidified when triturated with ether, yield of the title compound 32 g.

N.M.R. (CDCl$_3$): δ=8.0(d,2H); 7.4–7.2(m,7H); 3.75(s,2H); 3.7(s,2H); 3.1(s,3H) and 2.4(s,3H) ppm.

(B)

2-Hydroxy-N-methyl-2-(4-methanesulphonamidophenyl)ethylamine

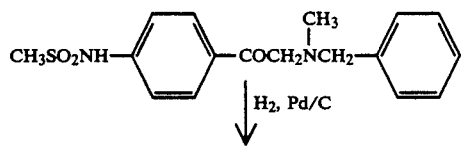

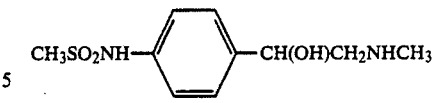

N-(4-Methanesulphonamidophenacyl)-N-methylbenzylamine (14.5 g) in ethanol (300 ml) containing 10% palladium on charcoal (2.0 g) was stirred under a hydrogen atmosphere (50 psi) at room temperature for 18 hours. Further catalyst (1.0 g) was added and hydrogenation was continued for a further 18 hours. The reaction was filtered and evaporated to afford an oil which was chromatographed on silica [Merck 'Kieselgel 60' (Trade Mark)], eluting with methylene chloride containing methanol (0% up to 20%) to give, after collection and evaporation of appropriate fractions, the title compound as a solid, yield 5 g. [Washing the column with methylene chloride:methanol:acetic acid (80:20:0.25) gave a further 4 g of the product as the acetate salt].

A portion of the title compound was recrystallised from acetonitrile, m.p. 150°–151°.

Analysis %: Found: C, 48.8; H, 6.6; N, 11.1; Calculated for C$_{10}$H$_{16}$N$_2$O$_3$S C, 49.2; H, 6.6; N, 11.5.

N.M.R. (CD$_3$OD): δ=7.3(q,4H); 4.75(dd,1H); 2.95(s,3H); 2.45(s,3H) ppm.

(C)

2-Hydroxy-2-(4-methanesulphonamidophenyl)-N-methyl-N-2-(5-phenyl-2H-pyridazin-3-on-2-yl)ethyl]ethylamine

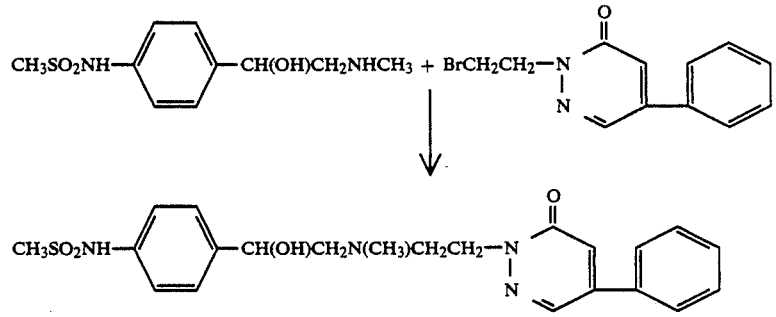

2-[5-Phenyl-2H-pyridazin-3-on-2-yl]ethyl bromide (0.28 g), 2-hydroxy-N-methyl-2-(4-methanesulphonamidophenyl)ethylamine (0.24 g) and triethylamine (0.22 g) were refluxed in ethanol (30 ml) for 4 hours. The solvent was removed and the residue taken up in methylene chloride, washed with water, evaporated and the residue chromatographed on silica [Merck 'Kieselgel 60' (Trade Mark)], eluting with ethyl acetate. Collection and evaporation of appropriate fractions gave the title compound as a solid which was recrystallised from diisopropyl ether, yield 0.1 g, m.p. 108°.

Analysis %: Found C,52.0; H,3.6; N,10.0; Calculated for C$_{22}$H$_{26}$N$_4$O$_4$S C,51.6; H,4.0; N, 10.0.

EXAMPLE 2

2-Hydroxy-2-(4-methanesulphonamidophenyl)-N-methyl-N-2-(5-benzyl-2H-pyridazin-3-on-2-yl)ethyl]ethylamine hydrochloride

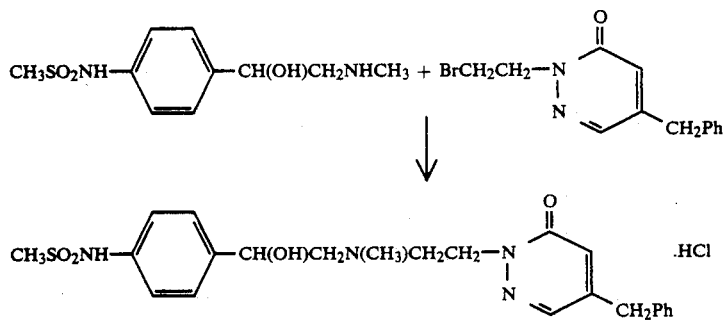

2-(5-Benzyl-2H-pyridazin-3-on-2-yl)ethyl bromide (0.58 g) [prepared analogously to the method of Example 3(A) hereinafter], 2-hydroxy-N-methyl-2-(4-methanesulphonamidophenyl)ethylamine (0.49 g) and triethylamine (0.22 g) were refluxed in ethanol for 2 hours. The solvent was removed and the residue taken up in methylene chloride and washed with aqueous sodium bicarbonate. The organic fraction was evaporated and the residue chromatographed on silica [Merck 'Kieselgel 60' (Trade Mark)] eluting with methylene chloride containing methanol (0% up to 2%) to afford, after collection and evaporation of appropriate fractions, an oil. The oil was dissolved in ethanol, diluted with ethereal hydrogen chloride and evaporated to dryness. The residue was triturated with ether to afford the title compound, yield 0.18 g.

Analysis %: Found C,55.8; H,5.7; N, 11.1; Calculated for $C_{23}H_{28}N_4O_4S.HCl$: C,56.0; H,6.0; N,11.4.

EXAMPLE 3

(A) 2-(4-Methyl-2H-phthalazin-1-on-2-yl)ethyl bromide

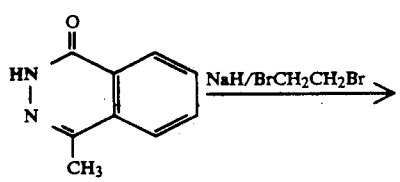

4-Methyl-(2H)-phthalazin-1-one (6 g) and sodium hydride (1.5 g, 60% in oil) in dimethylformamide (DMF) were stirred at room temperature until hydrogen evolution ceased. To this suspension was added a five fold excess of 1,2-dibromoethane (25 ml) and stirring was continued for a further 2 hours. The solvent was removed and the residue taken up in ethyl acetate, washed twice with brine, dried (MgSO4) and evaporated. Chromatography on silica [Merck 'Kieselgel 60' (Trade Mark)] eluting with methylene chloride containing methanol (0% up to 5%) gave, after collection and evaporation of appropriate fractions, a solid which was recrystallised from ethanol to give the title compound, yield 6.25 g, m.p. 102°-103°, used in the next stage.

(B)
2-(4-Methyl-2H-phthalazin-1-on-2-yl)-N-methylethylamine hydrobromide

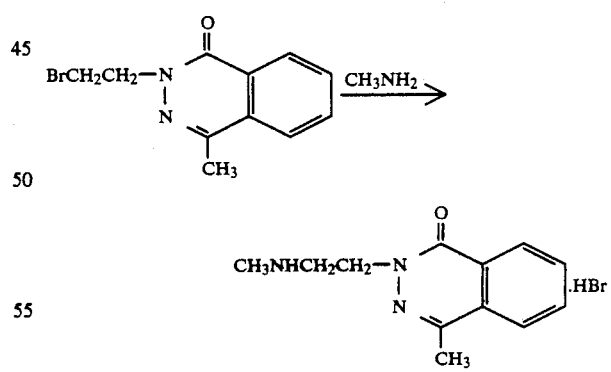

2-(4-Methyl-2H-phthalazin-1-on-2-yl)ethyl bromide (6.1 g) and methylamine (20 ml of 30% ethanolic methylamine) in ethanol (150 ml) were heated in a bomb at 100° for 2 hours. The solvent was removed and the residue triturated with ethyl acetate to give a yellow solid, which was recrystallised from ethanol to afford the title compound, yield 5.03 g, m.p. 219°-221°.

Analysis:
Found : C,48.2; H,5.3; N,14.1; Calculated for $C_{12}H_{15}N_3O.HBr$. : C,48.3; H,5.4; N 14.1.

(C)N-[4-Methanesulphonamidophenacyl]-N-methyl-2-(4-methyl-2H-phthalazin-1-on-2-yl)ethylamine hemihydrate

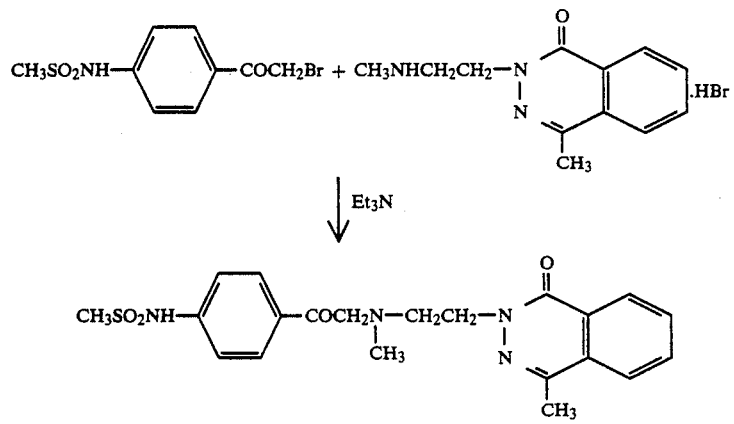

2-(4-Methyl-2H-phthalazin-1-on-2-yl)-N-methylethylamine hydrobromide (2 g),4-methanesulphonamidophenacyl bromide (1.8 g) and triethylamine (1.5 g) in ethanol (50 ml) were stirred at room temperature for 2 hours. The solvent was removed, the residue taken up in methylene chloride (100 ml), washed (aqueous sodium bicarbonate), dried (MgSO$_4$) and evaporated. Chromatography on silica [Merck 'Kieselgel 60' (Trade Mark)] eluting with methylene chloride containing methanol (0% up to 5%) gave, after collection and evaporation of appropriate fractions, an oil which was triturated with ethanol to give the title compound, yield 1.63 g, m.p. 176°–179°.

Analysis %: Found: C,58.0; H,5.6; N,12.6; Calculated for C$_{21}$H$_{24}$N$_4$O$_4$S.½H$_2$O: C,57.6; H,5.8; N,12.8.

EXAMPLES 4–17

The following compounds were prepared similarly to Example 3(C) by the following reaction:

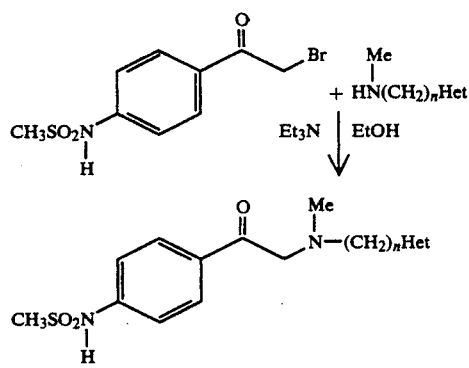

Example 4

N-[4-Methanesulphonamidophenacyl]-N-methyl-2-(2-phthalazin-1-on-2-yl) ethylamine hydrochloride

[Het = (structure)]

2-(2H-Phthalazin-1-on-2-yl)-N-methylethylamine (3.0 g), 4-methanesulphonamidophenacyl bromide (4.3 g) and triethylamine (2.2 g) in ethanol at room temperature for 16 hours gave the title compound, yield 1.3 g, m.p. 251°.

Analysis %: Found: C,53.4; ,H,5.2; N,12.9; Calculated for C$_{20}$H$_{22}$N$_4$O$_4$S.HCl: C,53.3; H,5.1; N,12.4.

Example 5

N-[4-Methanesulphonamidophenacyl]-N-methyl-2-(6-chloro-2H-isoindolin-1-on-2-yl)ethylamine hydrochloride

[Het = (structure)]

2-(6-Chloro-2H-isoindolin-1-on-2-yl)-N-methylethylamine (1.7 g), 4-methanesulphonamidophenacyl bromide (2.0 g) and triethylamine (1.45 g) in ethanol at room temperature for 16 hours gave the title compound as yellow solid, yield 0.7 g.

N.M.R. (CDCl$_3$): δ=7.0–8.0(m,7H); 4.4(s,2H); 3.82(s,2H); 3.78(t,2H); 3.08(s,3H); 2.85(t,2H); 2.50(s,3H)ppm.

EXAMPLE 6

N-[4-Methanesulphonamidophenacyl]-N-methyl-2-(2H-isoindolin-1-on-2-yl)ethylamine

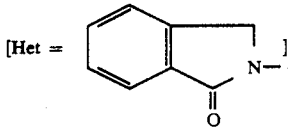

2-(2H-Isoindolin-1-on-2-yl)-N-methylethylamine (2.0 g), 4-methanesulphonamidophenacyl bromide (2.92 g) and triethylamine (1.45 g) in ethanol at room temperature for 16 hours gave the title compound as a yellow oil, yield 2.3 g.

N.M.R. (CDCl$_3$): δ=7.06–8.06(m,8H); 4.45(s,2H); 3.9(s,2H); 3.85(t,2H); 3.15(s,3H); 2.91(t,2H); 2.55(s,3H)ppm.

Example 7

N-[4-Methanesulphonamidophenacyl]-N-methyl-2-(3H-quinazolin-4-on-3-yl)ethylamine

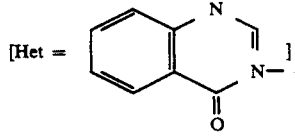

2-(3H-Quinazolin-4-on-3-yl)-N-methylethylamine (2.03 g), 4-methanesulphonamidophenacyl bromide (2.92 g) and triethylamine (1.1 g) in ethanol at room temperature for 16 hours gave the title compound as a colourless solid, yield 2.0 g.

N.M.R (CDCl$_3$): δ=7.02–8.3(m,9H); 4.12(t,2H); 3.81(s,2H); 3.07(s,3H); 2.97(t,2H); 2.50(s,3H)ppm.

Example 8

N-4-Methanesulphonamidophenacyl]-N-methyl-2-(2H-3,4-dihydroisoquinol-1-on-2-yl)ethylamine

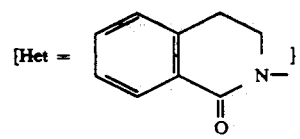

2-(2H-3,4-Dihydroisoquinol-1-on-2-yl)-N-methylethylamine (1.5 g), 4-methanesulphonamidophenacyl bromide (2.1 g) and triethylamine (2 g) in ethanol at room temperature for 18 hours gave the title compound as an oil, yield 1.7 g.

N.M.R. (CDCl$_3$): δ=8.3(d,1H); 7.9–6.95(m,8H); 6.35(d,1H); 4.1(t,2H); 3.8(s,2H); 2.95(m,5H); 2.4(s,3H)ppm.

Example 9

N-[4-Methanesulphonamidophenacyl]-N-methyl-2-(2H-isoquinol-1-on-2-yl)ethylamine

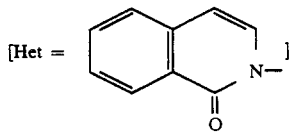

2-(2H-Isoquinol-1-on-2-yl)-N-methylethylamine (0.5 g), 4-methanesulphonamidophenacyl bromide (0.75 g) and triethylamine (0.8 g) in ethanol at room temperature for 18 hours gave the title compound as a yellow foam, yield 0.75 g.

N.M.R. (CDCl$_3$): δ=8.45(d,1H); 7.95–7.0(m,8H); 6.5(d,1H); 4.2(t,2H); 3.95(s,2H); 3.05(s,3H); 2.95(t,2H); 2.5(s,3H)ppm.

Example 10

N-[4-Methanesulphonamidophenacyl]-N-methyl-2-(1H-3,4-dihydroquinol-2-on-1-yl)ethylamine

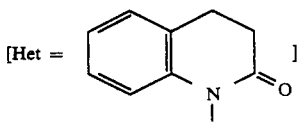

2-(1H-3,4-Dihydroquinol-2-on-1-yl)ethylamine(0.93 g), 4-methanesulphonamidophenacyl bromide (1.33 g) and triethylamine (1.36 g) in ethanol at room temperature for 18 hours gave the title compound as a yellow foam, yield 0.96 g.

Analysis %: Found: C,60.0; H,6.2; N,9.6; Calculated for C$_{21}$H$_{25}$N$_3$O$_4$S.$^1$/$_3$ EtOAc: C,60.3; H,6.3; N,9.45.

N.M.R. (CDCl$_3$): δ=8.05(d,2H); 7.4–7.0(m,4H); 4.15(t,2H); 3.9(s,2H); 3.1(s,3H); 2.8(m,6H); 2.5(s,3H).

Example 11

N-[4-Methanesulphonamidophenacyl]-methyl-2-(1H-3,4-dihydro-8-methylquinol-2-on-1-yl)ethylamine snd citrate salt

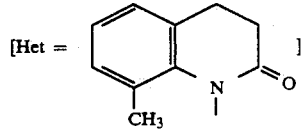

(A) 2-(1H-3,4-Dihydro-8-methylquinol-2-on-1-yl)ethylamine (0.9 g), 4-methanesulphonamidophenacyl bromide (1.2 g) and triethylamine (1.25 g) at room temperspture for 16 hours gave the title product as a foam, yield 0.43 g.

N.M.R. (CDCl$_3$)=: δ7.9(d,2H); 7.25(d,2H); 7.0(m,3H); 4.15(t,2H); 3.75(s,2H); 3.1(s,3H); 2.8(m,2H); 2.6(m,4H); 2.35(s,3H); 2.25(s,3H)ppm.

(B) A portion of the product of part (A) was treated with ethereal citric acid to give the citrate salt as a dihydrate.

Analysis %: Found: C,51.5; H,5.6; N,6.0; Calculated for C$_{22}$H$_{27}$N$_3$O$_4$S.C$_6$H$_8$O$_7$.2H$_2$O: C,51.1; H,6.0; N,6.4.

Example 12

N-[4-Methanesulphonamidophenacyl]-N-methyl-2-(1H-3,4-dihydro-4-methylquinol-2-on-1-yl)ethylamine

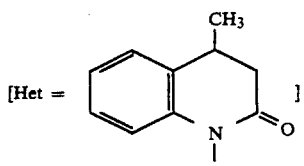

2-(1H-3,4-Dihydro-4-methylquinol-2-on-1-yl)-N-methylethylamine (1.47 g), 4-methanesulphonamidophenacyl bromide (1.97 g) and triethylamine (1.95 g) at room temperature for 18 hours gave the title compound as a foam, yield 1.3 g.

N.M.R. (CDCl$_3$): δ=8.05(d,2H); 7.4–7.0(m,6H); 4.2(m,2H); 3.95(s,2H); 3.1(m,5H); 2.8(m,3H); 2.5(s,3H); 1.3(d,3H)ppm

Example 13

N-(4-Methanesulphonamidophenacyl)-N-methyl-2-(benzoxszol-2-on-3-yl)ethylamine

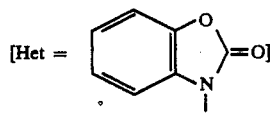

2-(Benzoxazol-2-on-3-yl)-N-methylethylamine (1.0 g), 4-methanesulphonamidophenacyl bromide (1.52 g) and sodium bicarbonate (0.5 g) in acetonitrile (50 ml) at room temperature for 18 hours gave the title compound, yield 0.2 g.

N.M.R. (CDCl$_3$): δ=7.65(d,2H); 6.8–7.2(m,7H); 3.6–4.0(m,4H); 2.8–3.1(m,5H); 2.5(s,3H)ppm.

Example 14

N-(4-Methanesulphonamidophenacyl)-N-methyl-2-(quinol-2-on-1-yl)ethylamine

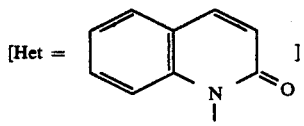

2-(Quinol-2-on-1-yl)-N-methylethylamine (0.15 g), 4-methanesulphonamidophenacyl bromide (0.22 g) and triethylamine (0.2 g) at room temperature for 18 hours gave the title compound as a foam, yield 0.16 g.

N.M.R. (CDCl$_3$): δ=7.95(d,2H); 7.15–7.7(m,7H); 6.65(d,1H); 4.5(t,2H); 3.95(s,2H); 3.1(s,3H); 2.85(t,2H); 2.55(s,3H).

Example 15

N-(4-Methanesulphonamidophenacyl)-N-methyl-2-(quinol-2-yl)ethylamine

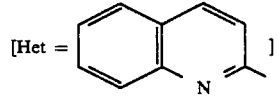

2-(Quinol-2-yl)-N-methylethylamine (0.37 g), 4-methanesulphonamidophenacyl bromide (0.58 g) and triethylamine (0.22 g) at room temperature for 18 hours gave the title compound as a thick oil, yield 0.3 g.

Example 16

N-(4-Methanesulphonamidophenacyl)-N-methyl-2-(indol-2-yl)ethylamine

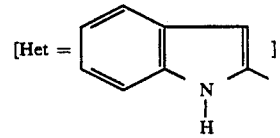

2-(Indol-2-yl)-N-methylethylamine (1.09 g), 4-methanesulphonamidophenacyl bromide (1.83 g) and triethylamine (1.9 g) at room temperature for 16 hours gave the title compound as a foam, yield 0.76 g.

N.M.R. (CDCl$_3$): δ=8.10–7.00(m,10H); 3.8(s,2H); 2.9(m,7H); 2.5(s,3H)ppm.

Example 17

N-(4-Methanesulphonamidophenacyl)-N-methyl-3-(2H-phthalazin-1-on-2-yl)propylamine

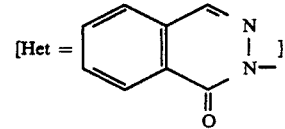

3-(2H-Phthalazin-1-on-2-yl)-N-methylpropylamine (0.75 g), 4-methanesulphonamidophenacyl bromide (1.0 g) and triethylamine (1.0 g) at room temperature for 16 hours gave the title compound as a foam, yield 0.57 g.

N.M.R. (CDCl$_3$): δ=8.4(d,1H); 8.2(s,1H); 8.1(d,2H); 7.8(m,3H); 7.25(d,2H); 4.3(t,2H); 3.8(s,2H); 3.1(s,3H); 2.65(t,2H); 2.35(s,3H); 2.1(quintet,2H)ppm.

The heterocyclic ethylamine starting material used in Example 4 was prepared as follows:

PREPARATION 1

(A)2-(2H-Phthalazin-1-on-2yl)-N-methyl-N-benzethylamine hydrochloride

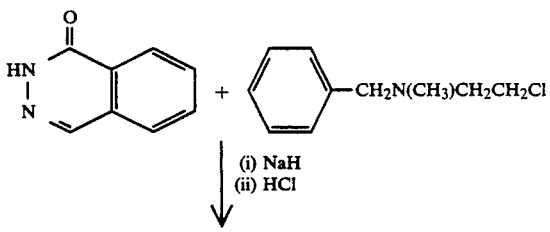

-continued

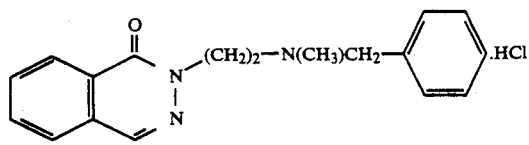

2H-Phthalazin-1-one (14.6 g) was stirred at 50° in dry dimethylformamide solution to which sodium hydride (4.5 g, 60% in oil) was added portionwise. After 4 hours N-benzyl-N-methyl-2chloroethylamine (18.35 g) was added to the reaction mixture and stirring was continued at 50° for 18 hours. The solvent was then removed and the residue partitioned between water and methylene chloride, the aqueous phase was extracted twice more with methylene chloride and the organic phases were combined and evaporated to give an oil. Chromatography of the oil on silica [Merck 'Kieselgel 60' (Trade Mark)] eluting with methylene chloride gave, after combination and evaporation of appropriate fractions, the free base of the product as a yellow oil (23.8 g). A portion of this oil (0.5 g) was dissolved in ether, ethereal hydrogen chloride was added, and the precipitate was collected and recrystallised from ethyl acetate/methanol to give the title compound, yield 0.45 g, m.p. 198°-200°.

Analysis %: Found: C,65.15; H,6.0; N,12.7; Calculated for $C_{18}H_{19}N_3O.HCl$: C,65.55; H,6.1; N,12.7.

(B)2-(2H-Phthalazin-1-on-2-yl)-N-methylethylaeine hydrochloride

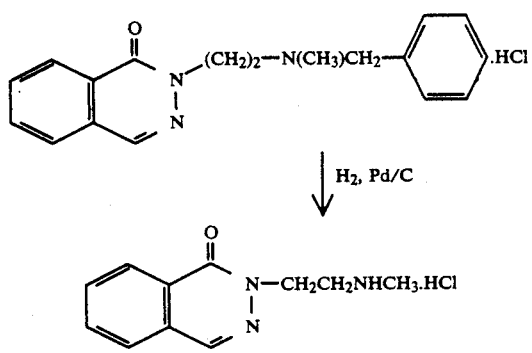

A solution of 2-(2H-phthalazin-1-on-2-yl)-N-methyl-N-benzylethylamine (41.5 g) in ethanol (1000 ml) and concentrated hydrochloric acid (50 ml) containing 5% palladium on charcoal (4.1 g) was stirred under a hydrogen atmosphere (50 p.s.i.) at room temperature for 18 hours. The reaction mixture was filtered and evaporated to afford a solid which was recrystallised from isopropanol to afford the title compound, yield 22.5 g, m.p.

Analysis %: 200°-201°. Found: C,55.0; H,5.8; N,17.3; Calculated for $C_{11}H_{13}N_3O.HCl$: C,55.1; H, 5.9; N, 17.5. H,5.9; N,17.5.

The heterocyclic ethylamine intermediates used in Examples 5 to 7 and 10 to 14, and the heterocyclic propylamine intermediate used in Example 17, were all prepared analogously to the method of Preparation 1 parts (A) and (B).

2-(2H-3,4-Dihydroisoquinol-1-on-2-yl)-N-methylethylamine used in Example 8 was prepared similarly to the procedure of Preparation 1 parts (A) and (B) except that isoquinol-1-one was used, the hydrogenation step (B) also converting the isoquinolonyl group to 3,4-dihydroisoquinolonyl.

The heterocyclic ethylamine starting material used in Example 9 was prepared analogously to the procedure of Example 3 parts (A) and (B).

The heterocyclic ethylamine starting materials used in Examples 15 and 16 are known compounds. The indole is commercially available and the quinoline is described in Monatsch. Chem., 83, 926 (1952).

Example 18

(A)

N-Methyl-N-(4-nitrophenethyl)-2-(2H-phthalazin-1-on-2-yl) ethylamine hydrochloride.

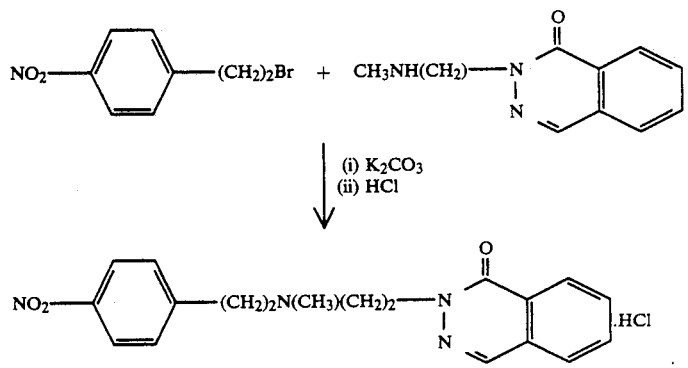

4-Nitrophenethyl bromide (9.21 g), (2H-phthalazin-1-on-2-yl)-N -methylethylamine (7.4 g) (see Preparation 1) and potassium carbonate (5.54 g) in acetonitrile (200 ml) were stirred at reflux for 48 hours. After evaporation to dryness, the product was partitioned between water and methylene chloride and the aqueous layer was extracted twice with methylene chloride. The organic extracts were combined, dried (MgSO4), filtered and evaporated to give a dark brown oil (12.8 g). This oil was dissolved in dry ether and an ethereal solution of hydrochloric acid was added until precipitation was complete. The resultant pale brown solid was crystallised from ethyl acetate/methanol to give the title compound as white crystals, yield 7.56 g, m.p. 204°-205°.

N.M.R. (CDCl3): δ=7.8-8.5 (m, 9H); 4.4 (t,2H); 3.0-3.7 (m,7H).

(B)
N-(4-Aminophenethyl)-N-methyl-2-(2H-phthalazin-1-on-2-yl) ethylamine.

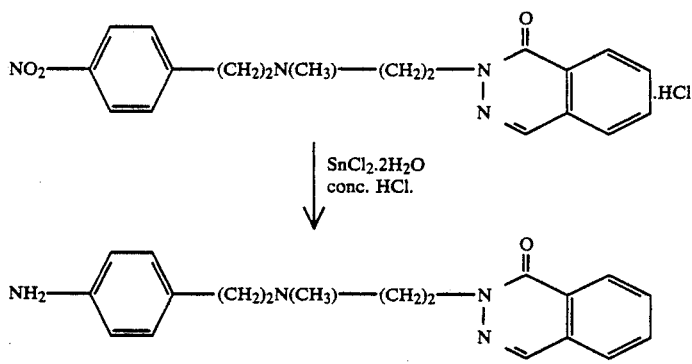

Stannous chloride dihydrate (13.05 g) was dissolved in concentrated hydrochloric acid and stirred at 55° C. N-Methyl -N-(4-nitrophenethyl)-2-(2H-phthalazin-1-on-2-yl)ethylamine hydrochloride (7.5 g) was added portionwise over 1 hour and the solution was then heated a further 4 hours at 100° C. The partly cooled solution was poured onto crushed ice containing 500 ml of a 20% aqueous solution of sodium hydroxide and then extracted three times with methylene chloride. The resultant organic extracts were combined, dried (MgSO$_4$), filtered and evaporated to give a pale yellow oil (6.0g). Chromatography of the oil on silica [Merck "Kieselgel 60" (Trade Mark)] eluting with methylene chloride gave, after collection and evaporation of appropriate fractions, the title compound as a pale yellow oil (3.5 g) which was used in part (C) without further purification.

(C)
N-(4-Methanesulphonamidophenethyl)-N-methyl-2-(2H-phthalazin -1-on-2-yl)ethylamine hydrochloride

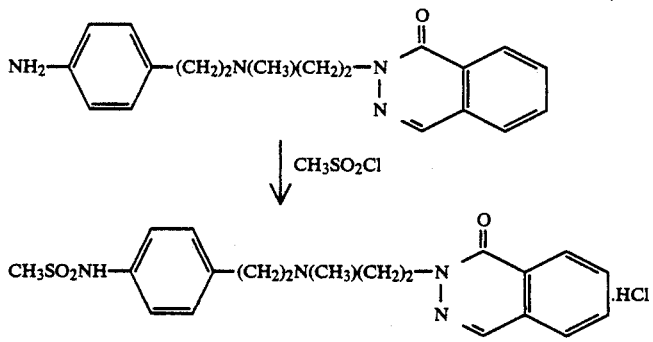

To a solution of N-(4-aminophenethyl)-N-methyl-2(2H-phthalazin-1-on-2-yl)ethylamine (2.0 g) in methylene chloride (15 ml) was added dropwise with stirring methanesulphonyl chloride (0.7 g). After stirring at room temperature for 16 hours, the product was evaporated to dryness to give a white solid (2.8 g). The solid was treated with sodium bicarbonate solution and the mixture extracted three tiees with methylene chloride. The combined organic extracts were dried (MgSO$_4$), filtered and evaporated to give a yellow oil (2.3 g). Chromatography of this oil on silica [Merck "Kieselgel 60" (Trade Mark)] eluting with ethyl acetate gave, after collection and evaporation of appropriate fractions, a colourless oil which was dissolved in dry ether. An excess of an ethereal hydrochloric acid solution was then added. The resultant precipitated solid, after drying, gave the title compound, yield 1.6 g, m.p. 158°–160

Analysis %: Found: C, 54.77; H, 6.06; N, 12.42; Calculated for C$_{20}$H$_{24}$N$_4$O$_3$S.HCl: C, 54.98; H, 5.77; N, 12.82.

EXAMPLES 19 AND 20

The following compounds were prepared similarly to the method of Example 18 part (C) using methanesulphonic anhydride in place of methanesulphonyl chloride.

Example 19

N-Ethyl-N-(4-methanesulphonamidophenethyl)-2-(2H-phthalazin-1-on -2-yl)ethylamine N-(4-Aminophenethyl)-N-ethyl-2-(2H-phthalazin-1-on-2-yl)ethylamine (320 mg.) and methanesulphonic anhydride (166 mg) in methylene chloride (10 ml) at room temperature for 16 hours gave the title compound, yield 140 mg., m.p. 101°–103°.

N.M.R. (CDCl$_3$) :-=δ=8.45(d,1H); 8.2(s,1H); 7.8 (m,3H); 7.15(q,4H); 4.35 (t,2H); 3.0–3.02 (m,5H); 2.75(m,6H); 1.05 (t,3H).

Example 20

N-(4-Methanesulphonamidophenethyl)-N-methyl-2-(1H-3,4-dihydroquinol-2-on-1-yl)ethylamine citrate N-(4-Aminophenethyl)-N-methyl-2-(1H-3,4-dihydroquinol-2-on-1-yl)ethylamine (520 mg) and methanesulphonic anhydride (280 mg) in methylene chloride (50 ml) at room temperature for 16 hours gave a colourless oil which when treated with ethereal citric acid gave the title compound.

N.M.R. (CDCl$_3$): δ=7.0–7.4 (m,8H); 4.3–4.45 (t,2H); 3.3–3.5 (m,4H); 2.6–3.2 (m,16H).

N-Ethyl-2-(2H-phthalazin-1-on-2-yl)ethylamine was prepared similarly to the method of Preparation 1 parts (A) and (B) using N-benzyl-N-ethyl-2-chloroethylamine, 2H-phthalazin-1-one and sodium hydride in dimethylformamide. N-(4-Aminophenethyl)-N-ethyl-2-(2H-phthalazin-1-on-2-yl) ethylamine, a starting material used in Example 19, was prepared similarly to the method of Example 18 parts (A) and (B) starting from N-ethyl-2-(2H-phthalazin-1-on-2-yl)ethylamine, 4-nitrophenethyl bromide and potassium carbonate.

N-Methyl-2-(1H-3,4-dihydroquinol-2-on-1-yl)ethylamine was prepared similarly to the method of preparation 1 parts (A) and (B) using N-benzyl-N-methyl-2-chloroethylamine, 1H-3,4-dihydroquinol-2-one and sodium hydride. N-(4-Aminophenethyl)-N-methyl-2-(1H-3,4-dihydroquinol-2-on-1-yl)ethylamine, a starting material used in Example 20, was prepared similarly to the method of Example 18 parts (A) and (B) starting from N-methyl-2-(1H-3,4-dihydroquinol-2-on-1-yl)ethylamine, 4-nitrophenethyl bromide and potassium carbonate.

EXAMPLE 21

N-[2-Hydroxy-2-(4-methanesulphonamidophenyl)ethyl]-N-methyl-2-(4-methyl-2H-phthalazin-1-on-2yl)ethylamine hydrochloride hemihydrate

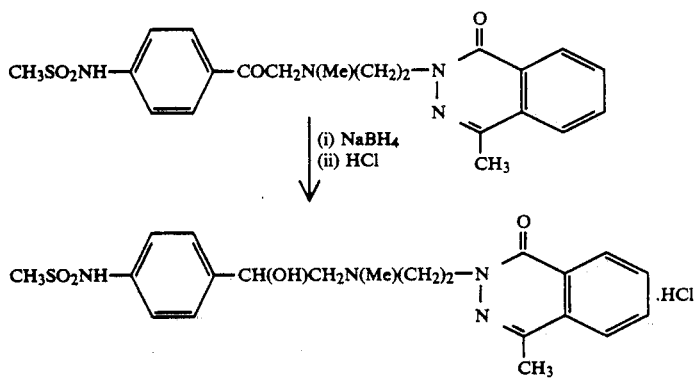

N-[4-Methanesulphonamidophenacyl]-N-methyl-2-(4-methyl-2H-phthalazin-1-on-2-yl)ethylamine hemihydrate (1.5 g) [see Example 3(C)] and sodium borohydride (2×200 mg pellets) in ethanol (50 ml) were stirred at room temperature overnight. The solvent was removed and the residue was taken up in methylene chloride (100 ml), diluted with 2M hydrochloric acid (25 ml), neutralized with sodium bicarbonate solution and the organic layer separated. The aqueous layer was extracted with methylene chloride (100 ml) and both organic layers were combined, washed with sodium bicarbonate, dried (MgSO$_4$) and evaporated to give a yellow oil. Chromatography of this oil on silica [Merck "Kieselgel 60" (Trade Mark)] eluting with methylene chloride containing methanol (0% up to 5%) followed by collection and evaporation of appropriate fractions gave the desired product as an oil which was taken up in ethyl acetate. Addition of ethereal hydrogen chloride gave the title compound which was collected by filtration and dried in vacuo, yield 1.35 g, m.p; 154°–157°.

Analysis %: Found: C,53.0; H,5.8; N, 11.7 Calculated for C$_{21}$ H$_{26}$N$_4$O$_4$S.HCl.½H$_2$O:C,53.0; H,5.9; N, 11.8

EXAMPLES 22–34

The following compounds were prepared similarly to the previous Example by the following reaction:

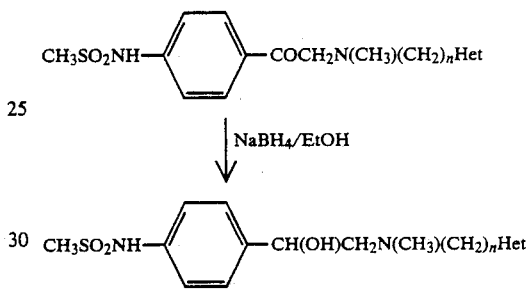

[n = 2, Examples 22–23 and n = 3, Example 34]

Solvent content in these products was determined by high field n.m.r.

| Example No. | Het | n | Form Isolated | m.p. (°C.) | Analysis % (Theoretical in brackets) | | |
|---|---|---|---|---|---|---|---|
| | | | | | C | H | N |
| 22 | ![structure] | 2 | Hydrochloride | 174 | 55.25 | 5.8 | 11.6 (11.9) |

-continued

| Example No. | Het | n | Form Isolated | m.p. (°C.) | Analysis % (Theoretical in brackets) C | H | N |
|---|---|---|---|---|---|---|---|
| 23 | (2,3-dihydro-1-oxo-isoindol-2-yl) | 2 | Hydrochloride | 104 | 54.1 (54.6 | 5.8 6.0 | 9.6 9.55) |
| 24 | (5-chloro-2,3-dihydro-1-oxo-isoindol-2-yl) | 2 | Hydrochloride | 138 | 50.4 (50.6 | 5.4 5.3 | 8.7 8.9) |
| 25 | (3-methyl-4-oxo-3,4-dihydroquinazolin-3-yl) | 2 | Free Base | 174 | 57.2 (57.7 | 5.8 5.8 | 13.2 13.45) |
| 26 | (2-methyl-1-oxo-1,2,3,4-tetrahydroisoquinolin-2-yl) | 2 | Hydrochloride Hydrate | Isolated as as foam | 53.7 (53.4 | 6.1 6.4 | 8.8 8.9) |
| 27 | (2-methyl-1-oxo-1,2-dihydroisoquinolin-2-yl) | 2 | Free Base (containing ¼ Mole of CH$_2$Cl$_2$) | Isolated as a foam | 59.1 (59.5 | 6.1 6.15 | 10.1 9.9) |
| 28 | (1-methyl-2-oxo-1,2,3,4-tetrahydroquinolin-1-yl) | 2 | Citrate Sesquihydrate (contains 1/5 mole EtOAc) | Isolated as as foam | 51.6 (51.85 | 6.0 6.3 | 6.15 6.4) |
| 29 | (1-methyl-4-methyl-2-oxo-1,2,3,4-tetrahydroquinolin-1-yl) | 2 | Free Base Hemihydrate | Isolated as a foam | 59.5 (59.1 | 7.2 6.8 | 9.4 9.4) |
| 30 | (1,8-dimethyl-2-oxo-1,2,3,4-tetrahydroquinolin-1-yl) | 2 | Free Base Hemihydrate ¼ ethyl acetate | Isolated as a foam | 59.7 (60.4 | 7.0 6.8 | 9.1 9.0) |
| 31 | (2-methylquinolin-2-yl) | 2 | Dihydrochloride Hydrate | 150–151 | 51.1 (51.4 | 5.7 6.0 | 8.6 8.6) |
| 32 | (3-methyl-2-oxo-2,3-dihydrobenzoxazol-3-yl) | 2 | Free Base (containing ¼ Mole of CH$_2$Cl$_2$) | Isolated as a foam | 53.1 (53.2 | 5.6 5.55 | 10.2 9.85) |

-continued

| Example No. | Het | n | Form Isolated | m.p. (°C.) | Analysis % (Theoretical in brackets) C | H | N |
|---|---|---|---|---|---|---|---|
| 33 | 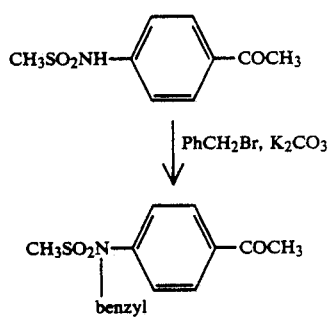 | 2 | Free Base (containing ½ Mole CH₂Cl₂) | Isolated as a foam | 59.6 (59.5 | 6.0 6.3 | 10.0 10.3) |
| 34 | 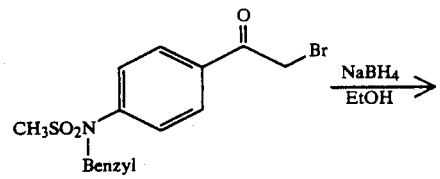 | 3 | Free Base (containing ½ Mole CH₂Cl₂) | Isolated as a foam | 58.0 (57.5 | 5.95 6.00 | 12.6 12.7) |

EXAMPLE 35 (ALTERNATIVE TO EXAMPLE 22)

(A) 4-[N-Benzylmethanesulphonamido]acetophenone

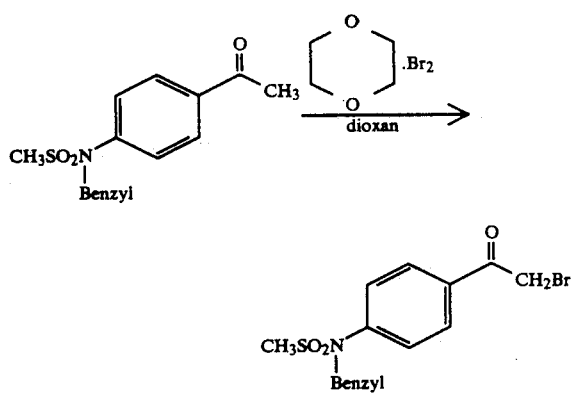

4-(Methanesulphonaeido)acetophenone (50 g), benzyl bromide (40.1 g) and potassium carbonate (32.5 g) in methyl ethyl ketone were stirred at reflux temperature for 4 hours. After cooling the solvent was evaporated and the residue was taken up in methylene chloride and washed twice with water, three times with 2M sodium hydroxide and twice with brine. The organic layer was dried and evaporated to give a solid which was triturated with ether and recrystallised from ethyl acetate to give the title compound, yield 62 g, m.p. 122°-123°.

Analysis %: Found:C,63.7; H,5.6; N,4.7; Calculated for $C_{16}H_{17}NO_3S$ :C,63.3; H,5.65; N,4.6.

(B) 4-[N-Benzylmethanesulphonamido]phenacyl bromide

Dioxan dibromide (8.18 g) in dioxan (50ml) and diethyl ether (30ml) was added dropwise to a stirred suspension of 4-[N-benzylmethanesulphonamido]acetophenone (10 g) in dioxane (200ml) at room temperature and stirring was continued for a further 2 hours. The solvent was then removed and the resulting oil was triturated with diethyl ether, cooled and the colourless solid was filtered off. Recrystallisation of the solid from ethyl acetate/hexane gave the title compound, yield 7.3g, m.p. 101°-103°.

Analysis: Found: C,50.6; H,4.1; N,3.5; Calculated for $C_{16}H_{16}BrNO_3S$ :C,50.3; H,4.2; N,3.7.

(C) 2-[4-N-Benzylmethanesulphonamido)phenyl]oxirane

4-[N-Benzylmethanesulphonamido]phenacyl bromide (30 g) and sodium borohydride (4 g) in ethanol (500 ml) were stirred at room temperature for 18 hours. The solvent was then removed and the residue was taken up in ethyl acetate and washed three times with sodium bicarbonate solution and three times with brine. The organic phase was dried and evaporated to give an oil which was chromatographed on silica, "Kieselgel 60" (Merck, Trade Mark), eluting with methylene chloride. The product-containing fractions were combined and evaporated to give a solid which was triturated with hexane and filtered off to give the title compound, yield 13 g, m.p. 89°-92°.

Analysis: Found:C,63.1; H,5.4; N,4.5; Calculated for $C_{16}H_{17}NO_3S$:C,63.3; H,5.65; N,4.6.

(D)

N-[2-(4-{-N-Benzylmethanesulphonamido}phenyl)-2-hydroxyethyl]-N-methyl-2-(phthalazin-1-on-2-yl)ethylamine

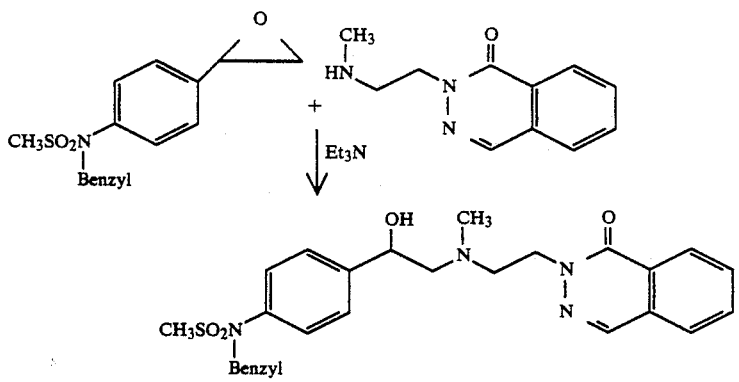

2-[4-(N-Benzylmethanesulphonamido)phenyl]oxirane (1.5 g), N-methyl-2-(phthalazin-1-on-2-yl)ethylamine (1.4 g) and triethylamine (1.4 g) in isopropanol (50 ml) were stirred at reflux temperature for 5 hours. The solvent was evaporated, the residue dissolved in methylene chloride and washed three times with sodium carbonate solution and three times with brine. The organic layer was dried and evaporated to give an oil which was purified by column chromatography on silica, "Kieselgel 60" (Merck, Trade Mark), eluting with methylene chloride containing methanol (0% up to 2%). Combination and evaporation of the appropriate fractions gave a foam which was chromatographed a second time on silica, "Kieselgel 60" (Merck, Trade Mark), eluting with methyl isobutyl ketone (MIBK) containing acetone (0% up to 20%). The appropriate fractions were combined and evaporated then re-evaporated from diethyl ether to give the title compound as a foam, yield 450 mg.

Analysis: Found:C,63.6; H,6.0, N,10.45. Calculated for $C_{27}H_{30}N_4O_4S$+solvent*: C,63.7; H,6.1; N,10.7.
*contains solvent 1/12 MIBK, 1/20 $CH_2Cl_2$ and 1/20 $Et_2O$ as judged by $^1H$—n.m.r.

(E)

N-[2-(4-Methanesulphonamidophenyl)-2-hydroxyethyl]-N-methyl-2-(phthalazin-1-on-2-yl)ethylamine

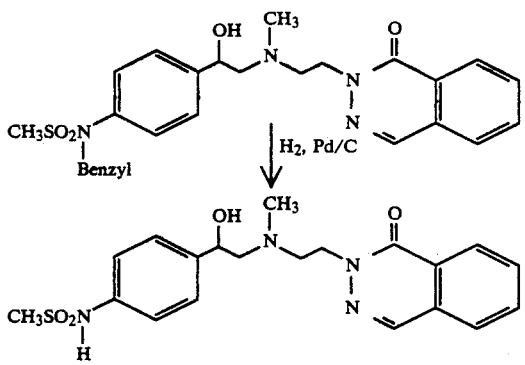

N-[2-(4-{N-Benzylmethanesulphonamido}phenyl)-2-hydroxyethyl]-N-methyl-2-(phthalazin-1-on-2-yl)ethylamine (0.4 g—as solvate from part (D) in ethanol (50 ml) containing 5% Pd/C (0.1 g) was stirred under a hydrogen atmosphere (50 p.s.i.) at 50° for 18 hours. The reaction mixture was then filtered and the ethanol removed. The residue was dissolved in methylene chloride and washed three times with sodium bicarbonate solution and three times with brine. The organic layer was dried and evaporated to give an oil which was purified by column chromatography on silica, "Kieselgel 60" (Merck, Trade Mark), eluting with methylene chloride containing methanol (0% up to 2%). The appropriate fractions were combined and evaporated to give an oil which solidified after stirring for 14 hours in diethyl ether, filtration giving the title compound, 0.11 g, m.p. 134°-137°.

Analysis %: Found:C,57.8; H,5.9; N,13.3; Calculated for $C_{20}H_{24}N_4O_4S.1/6Et_2O$*: C,57.9; H, 6.03; N,13.1
*Solvate as determined by $^1H$—n.m.r.

EXAMPLE 36

(A)

O-Methanesulphonyl-4-methanesulphonamidophenethyl alcohol

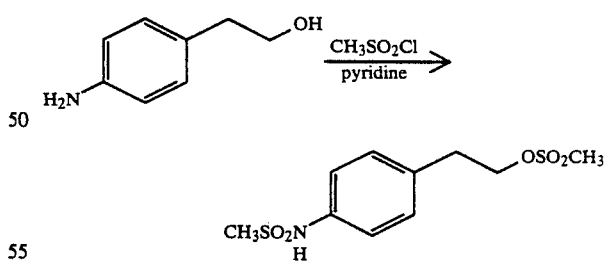

Methanesulphonyl chloride (73.3 g, 0.64 mole) was added dropwise to a stirred solution of 4-aminophenethyl alcohol (41.15 g, 0.3 mole) in pyridine (350 ml) whilst maintaining the reaction at 0°-5°. After the addition was complete, stirring was continued at 0° for 30 minutes and then room temperature for 2 hours. The reaction mixture was poured in water, the precipitate collected by filtration, washed with water and then recrystallised from ethyl acetate to give the title compound, yield 55.9 g, m.p. 135°-137°.

Analysis %: Found: C,40.6; H,5.2; N,4.9; Calculated for $C_{10}H_{15}NO_5S_2$: C,40.9; H,5.15; N,4.8.

(B)
N-Methyl-N-(4-methanesulphoneamidophenethyl)-2-(quinol-2-yl)ethylamine dihydrochloride

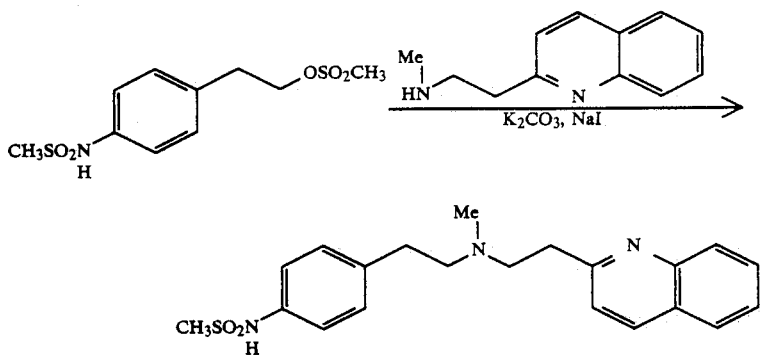

O-Methanesulphonyl-4-methanesulphonamidophenethyl alcohol (1.47 g), N-methyl-2-(quinol-2-yl)ethylamine (0.94 g), potassium carbonate (1.6 g) and sodium iodide (0.74 g) were heated at reflux in acetonitrile (35 ml) for 17 hours. The reaction mixture was cooled, filtered and the filtrate was evaporated to dryness in vacuo. The residue was dissolved in ethyl acetate, washed with water and then 2M hydrochloric acid. The acid layer was made basic with aqueous sodium carbonate (pH=8) and extracted with ethyl acetate; this organic layer was evaporated in vacuo and the resultant oil purified by column chromatography on silica eluting with methylene chloride containing methanol (3% up to 5%). The product-containing fractions were combined and evaporated in vacuo and the residue was taken up in ethyl acetate, diluted with ethereal hydrogen chloride and the precipitate collected by filtration, washed with ether and dried to give the title compound, yield 0.27 g. Because the compound was hygroscopic no accurate melting point could be recorded.

Analysis %: Found C,54.8; H,6.0; N,8.8; Calculated for $C_{21}H_{25}N_3O_2S.2HCl$: C, 55.3; H,6.0; N,9.2.

We claim:

1. A sulfonamide compound of the formula:

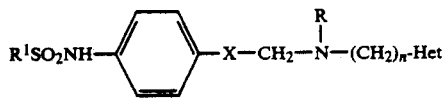

or a pharmaceutically acceptable salt thereof, wherein R and $R^1$ are each $C_1$–$C_4$ alkyl;
X is —$CH_2$—, —CO— or —CH(OH)—;
n is two, three or four; and
"Het" is a nitrogen-containing heterocyclic group of the formula:

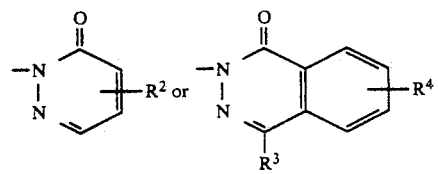

wherein $R^2$ is phenyl or benzyl; and $R^3$ and $R^4$ are each hydrogen, halogen or $C_1$–$C_4$ alkyl.

2. A compound as claimed in claim 1 wherein "Het" is 5-phenyl-2H-pyridazin-3-on-2-yl, 5-benzyl-2H-pyridazin-3-on-2-yl, 4-methyl-2H-phthalazin-1-on-2-yl or 2H-phthalazin-1-on-2-yl.

3. A compound as claimed in claim 1 wherein R is methyl, $R^1$ is methyl or ethyl and n is two or three.

4. A compound as claimed in claim 3 wherein $R^1$ is methyl, n is two and X is —$CH_2$— or —CH(OH)—.

5. N-[2-(4-Methanesulphonamidophenyl)-2-hydroxyethyl]-N-methyl-2-(2H-phthalazin-1-on-2-yl)ethylamine.

6. A pharmaceutical composition comprising a pharmaceutically acceptable carrier or diluent and an effective anti-arrhythmic amount of a compound as claimed in claim 1.

7. A method for preventing or reducing cardiac arrhythmias in the treatment of a subject afflicted with an impaired cardiac pump function, which comprises administering to said subject an effective anti-arrhythmic amount of a compound as claimed in claim 1.

8. A compound as claimed in claim 1 wherein "Het" is 5-phenyl-2H-pyridazin-3-on-2-yl, 5-benzyl-2H-pyridazin-3-on-2-yl, 4-methyl-2H-phthalazin-1-on-2-yl or 2H-phthalazin-1-on-2-yl, R and $R^1$ are each methyl, n is two and x is —CH(OH)—.

* * * * *